United States Patent
Osumi

(10) Patent No.: US 9,173,629 B2
(45) Date of Patent: Nov. 3, 2015

(54) ULTRASONIC DIAGNOSTIC APPARATUS AND ULTRASONIC IMAGE PROCESSING APPARATUS

(75) Inventor: Ryota Osumi, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1303 days.

(21) Appl. No.: 12/944,305

(22) Filed: Nov. 11, 2010

(65) Prior Publication Data

US 2011/0118599 A1 May 19, 2011

(30) Foreign Application Priority Data

Nov. 18, 2009 (JP) .................................. 2009-263181

(51) Int. Cl.
- A61B 8/00 (2006.01)
- G01S 7/52 (2006.01)
- G01S 15/89 (2006.01)

(52) U.S. Cl.
CPC .............. *A61B 8/00* (2013.01); *G01S 7/52077* (2013.01); *G01S 15/8977* (2013.01)

(58) Field of Classification Search
CPC ............ A61B 8/00; A61B 5/204; A61B 8/08; A61B 8/488; A61B 5/0456; G01S 15/8977; G01S 7/52077; G01R 33/54

USPC .......................... 600/407, 437, 441, 443, 447
See application file for complete search history.

(56) References Cited

U.S. PATENT DOCUMENTS

| | | | |
|---|---|---|---|
| 2008/0181479 A1* | 7/2008 | Yang et al. ..................... | 382/131 |
| 2008/0212887 A1* | 9/2008 | Gori et al. ..................... | 382/248 |
| 2011/0044524 A1* | 2/2011 | Wang et al. ................... | 382/131 |

FOREIGN PATENT DOCUMENTS

JP    2009-82469    4/2009

* cited by examiner

*Primary Examiner* — Unsu Jung
*Assistant Examiner* — Joel Lamprecht
(74) *Attorney, Agent, or Firm* — Oblon, McClelland, Maier & Neustadt, L.L.P.

(57) ABSTRACT

Certain embodiments provide an ultrasonic diagnostic apparatus including a data acquisition unit configured to acquire a plurality of spatially overlapping ultrasonic images or a plurality of temporarily consecutive ultrasonic images, a block extraction unit configured to extract, for each pixel, a block having a predetermined size and including each pixel as a central pixel for each of the plurality of ultrasonic images, a covariance calculation unit configured to calculate a covariance for each pixel of each of the plurality of ultrasonic images by using the block for each pixel, and a generating unit configured to generate a synthesized image using the plurality of ultrasonic images and to control a level of each pixel of the synthesized image based on a covariance of each pixel of each of the plurality of ultrasonic images.

21 Claims, 11 Drawing Sheets

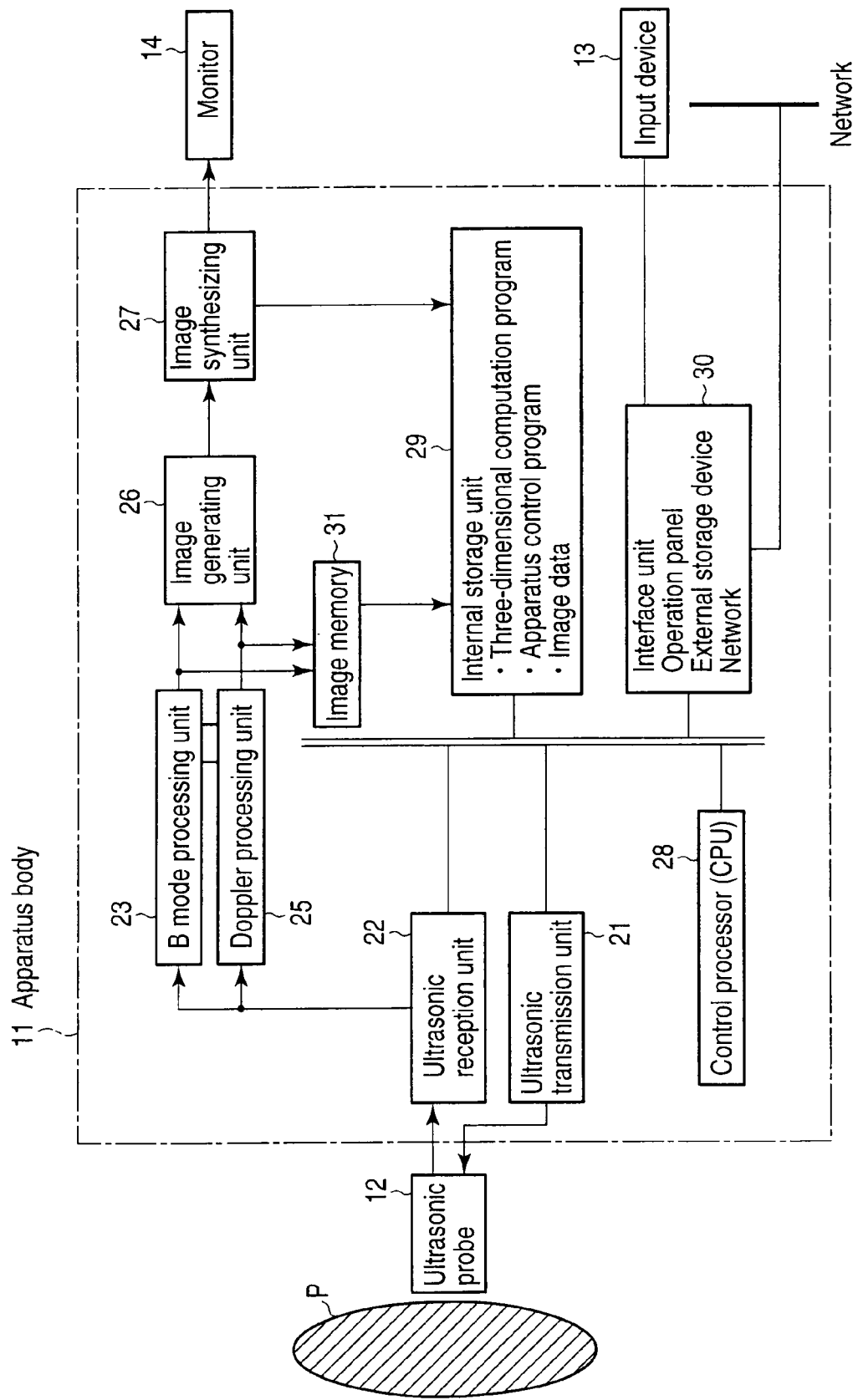
F I G. 1

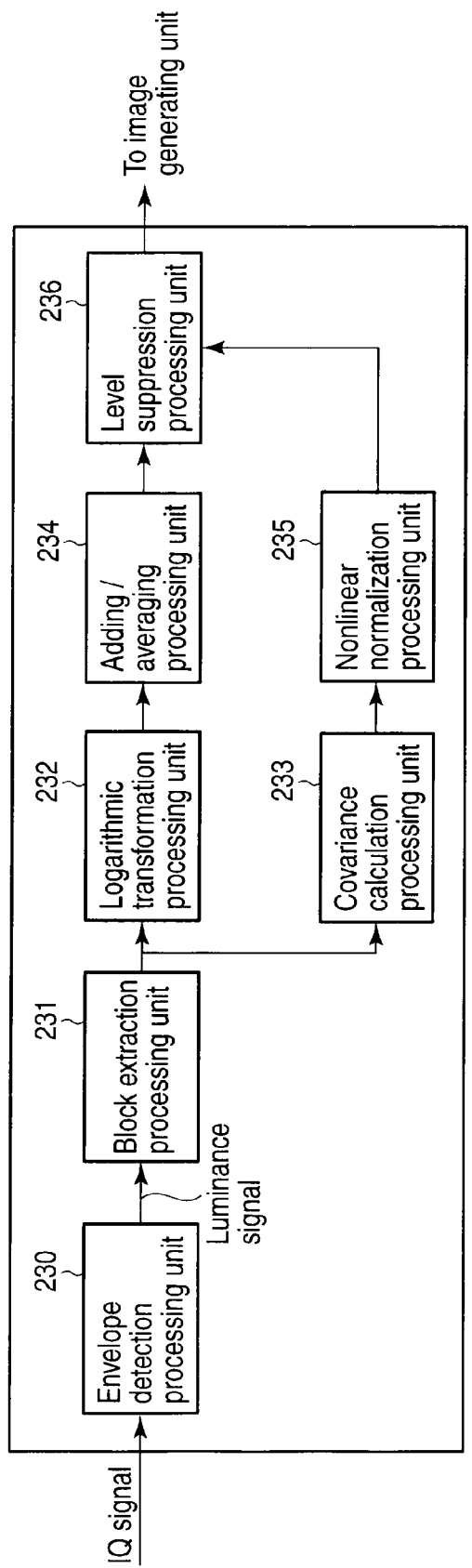
F I G. 2

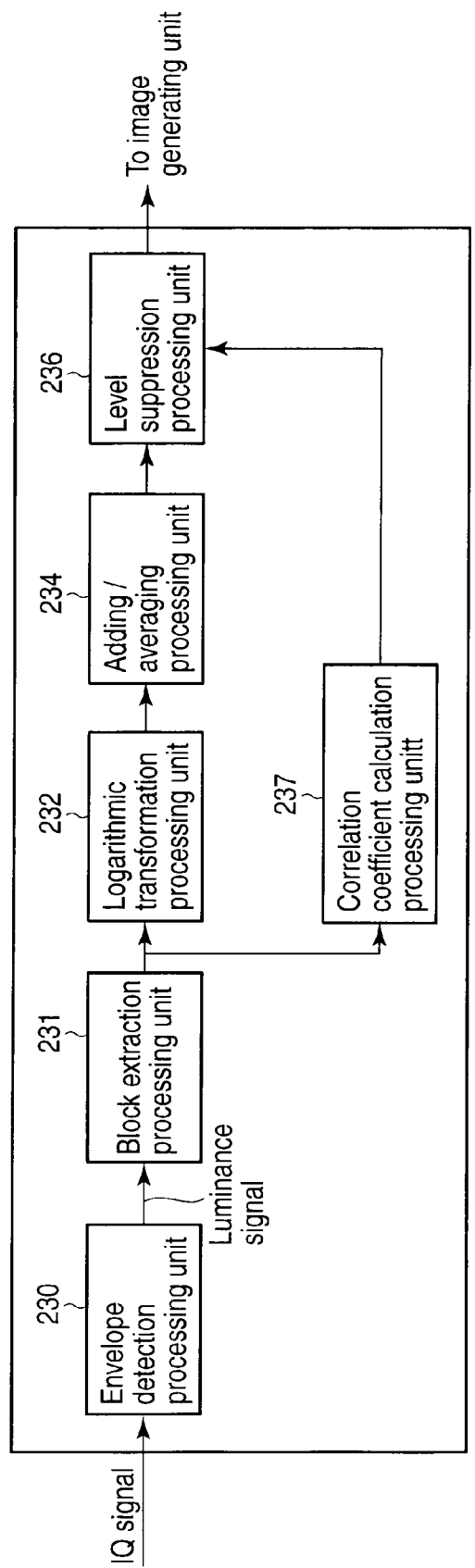
F I G. 5

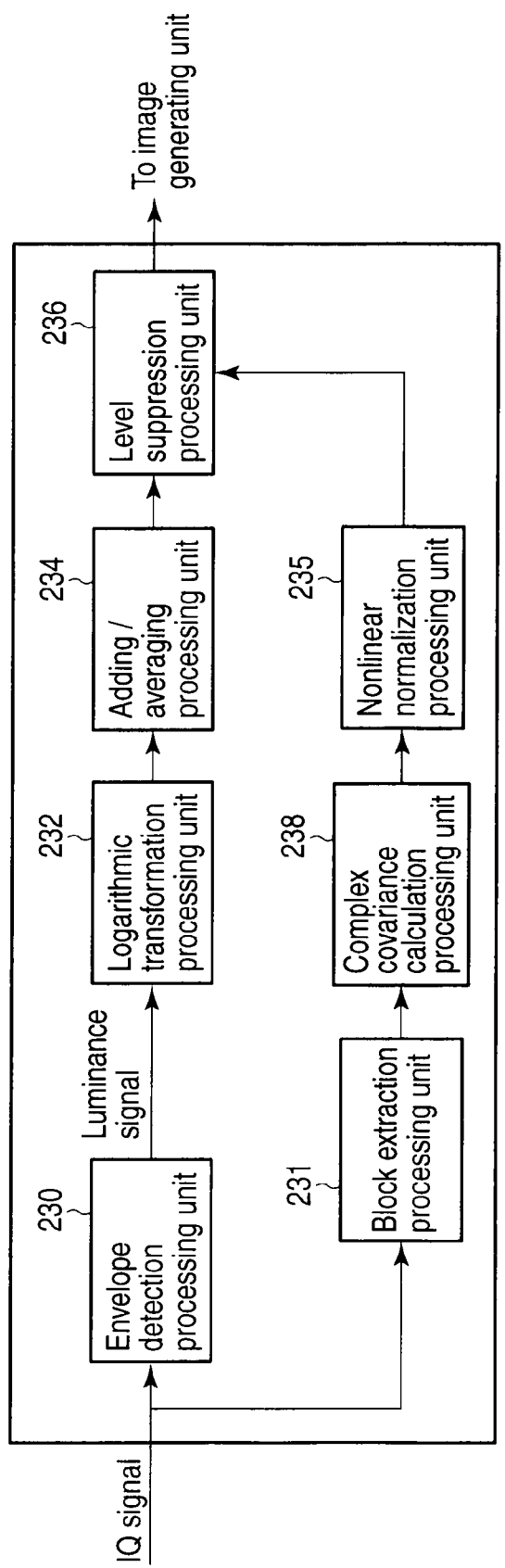
F I G. 6

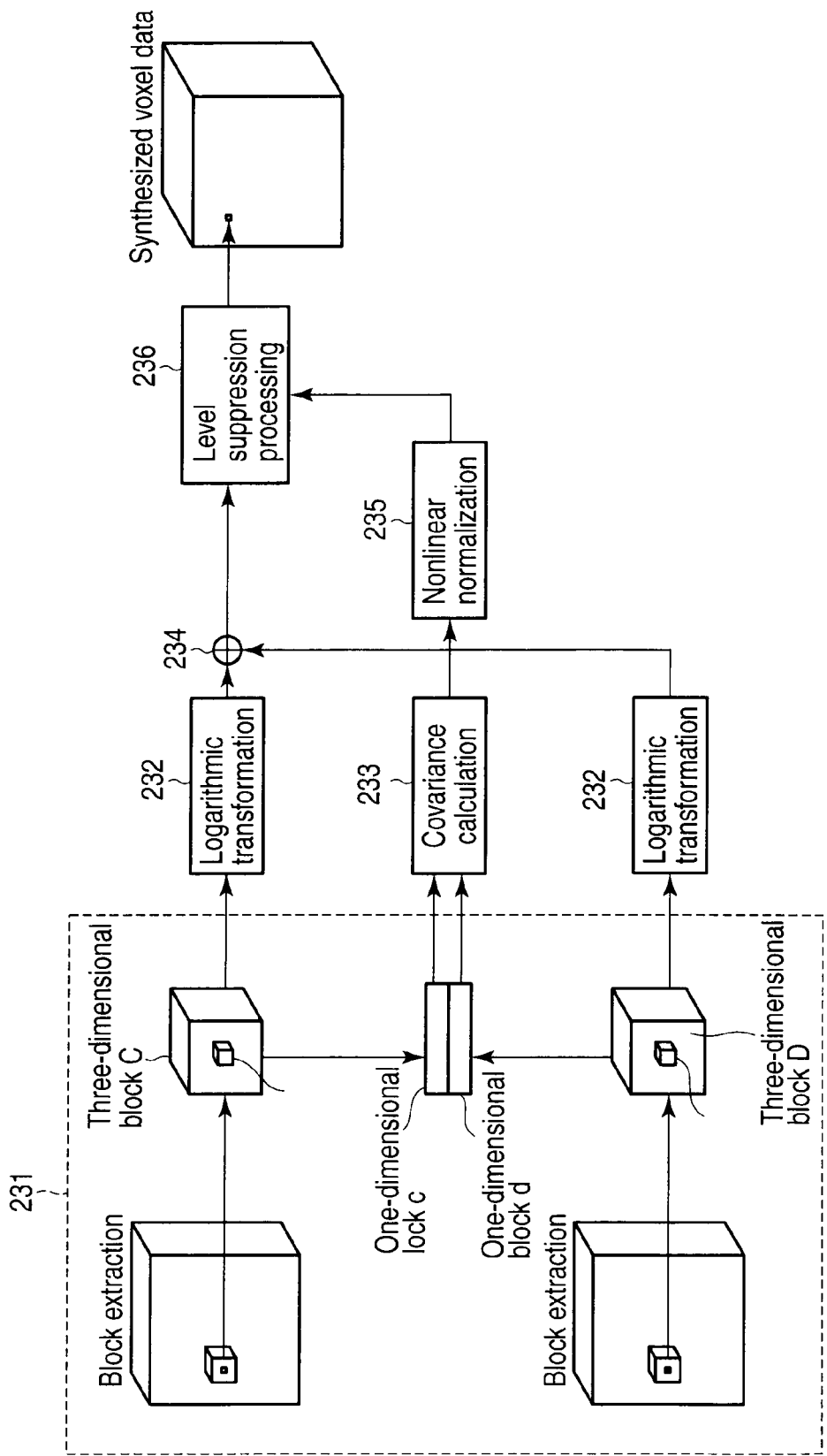
F I G. 11

US 9,173,629 B2

ULTRASONIC DIAGNOSTIC APPARATUS AND ULTRASONIC IMAGE PROCESSING APPARATUS

CROSS-REFERENCE TO RELATED APPLICATIONS

This application is based upon and claims the benefit of priority from Japanese Patent Application No. 2009-263181, filed Nov. 18, 2009; the entire contents of which are incorporated herein by reference.

FIELD

Embodiments described herein relate generally to an ultrasonic diagnostic apparatus and an ultrasonic image processing apparatus.

BACKGROUND

In ultrasonic diagnosis, the pulsation of the heart or the movement of a fetus can be displayed in real time by the simple operation of bringing an ultrasonic probe into contact with the surface of the body. In addition, this technique is highly safe, and hence allows repetitive examination. Furthermore, this system is smaller in size than other diagnostic apparatuses such as X-ray, CT, and MRI apparatuses. This technique can therefore be said to be a simple diagnostic technique which facilitates examination to be performed by moving the apparatus to the bed side. Ultrasonic diagnostic apparatuses used in this ultrasonic diagnosis vary in type depending on the functions which they have. Some compact apparatuses which have already been developed are small enough to be carried with one hand, and ultrasonic diagnosis is free from the influence of radiation exposure unlike diagnosis using X-rays. Therefore, such ultrasonic diagnostic apparatuses can be used in obstetric treatment, treatment at home, and the like.

For ultrasonic diagnostic diagnosis, recently, an ultrasonic diagnostic apparatus capable of generating and displaying three-dimensional image data has been implemented by using such an ultrasonic diagnostic apparatus. Such an ultrasonic diagnostic apparatus two-dimensionally or three-dimensionally scans ultrasonic waves using an ultrasonic probe having ultrasonic transducers arranged one-dimensionally or two-dimensionally to generate an image corresponding to a two-dimensional region (slice) or three-dimensional region (volume). The apparatus then displays the generated image as a two-dimensional image or three-dimensional image. A doctor observes the displayed ultrasonic image and performs image diagnosis of an affected part.

The image obtained by the ultrasonic diagnostic apparatus contains various kinds of noise and speckle caused by the interference phenomenon of received ultrasonic signals, which often hinder the accurate observation of the position and shape of the boundary of an object tissue. Recently, therefore, various types of processing methods for the reduction of such noise and speckle have been proposed. Typical examples of such methods include the spatial compound method and the persistence method. The spatial compound method is a method of reducing noise and speckle by dividing the reception aperture of a probe into a plurality of patterns and acquiring and adding the amplitudes of a plurality of reception signals corresponding to the respective patterns. The persistence method is a method of reducing noise and speckle by performing weighted addition of the images of a plurality of frames including the current and temporarily consecutive frames and using the result for display.

Consider each image before the processing of reducing noise and speckle. Noise having no correlation with (i.e., independent of) other images is generated. When considering noise which is independently generated in each image, it can be said that averaging operation in the spatial compound method uses the phenomenon that a noise component decreases in proportion to the reciprocal of the square root of the number of times of addition of signal components. Weighted addition in the persistence method aims at the same effect.

The conventional ultrasonic diagnostic apparatus has, for example, the following problem.

That is, methods of reducing noise and speckle, typified by the spatial compound method and the persistence method, uniformly perform addition processing regardless of the positions of the pixels of an image. For this reason, noise is not sufficiently reduced in a portion (pixel), of an image, which is mostly constituted by noise.

BRIEF DESCRIPTION OF THE DRAWINGS

FIG. 1 is a block diagram showing the arrangement of an ultrasonic diagnostic apparatus according to the first embodiment;

FIG. 2 is a block diagram showing an example of the arrangement of a B mode processing unit 23 to implement a noise reduction function using covariances according to the first embodiment;

FIG. 5 is a block diagram showing an example of the arrangement of a B mode processing unit 23 to implement a noise reduction function using correlation coefficients according to the second embodiment;

FIG. 6 is a block diagram showing an example of the arrangement of a B mode processing unit 23 to implement a noise reduction function using covariances according to the third embodiment;

FIG. 11 is a conceptual view for explaining a procedure for noise reduction processing using the covariances of three-dimensional image data, which is executed by a B mode processing unit 23.

DETAILED DESCRIPTION

Figure 3:
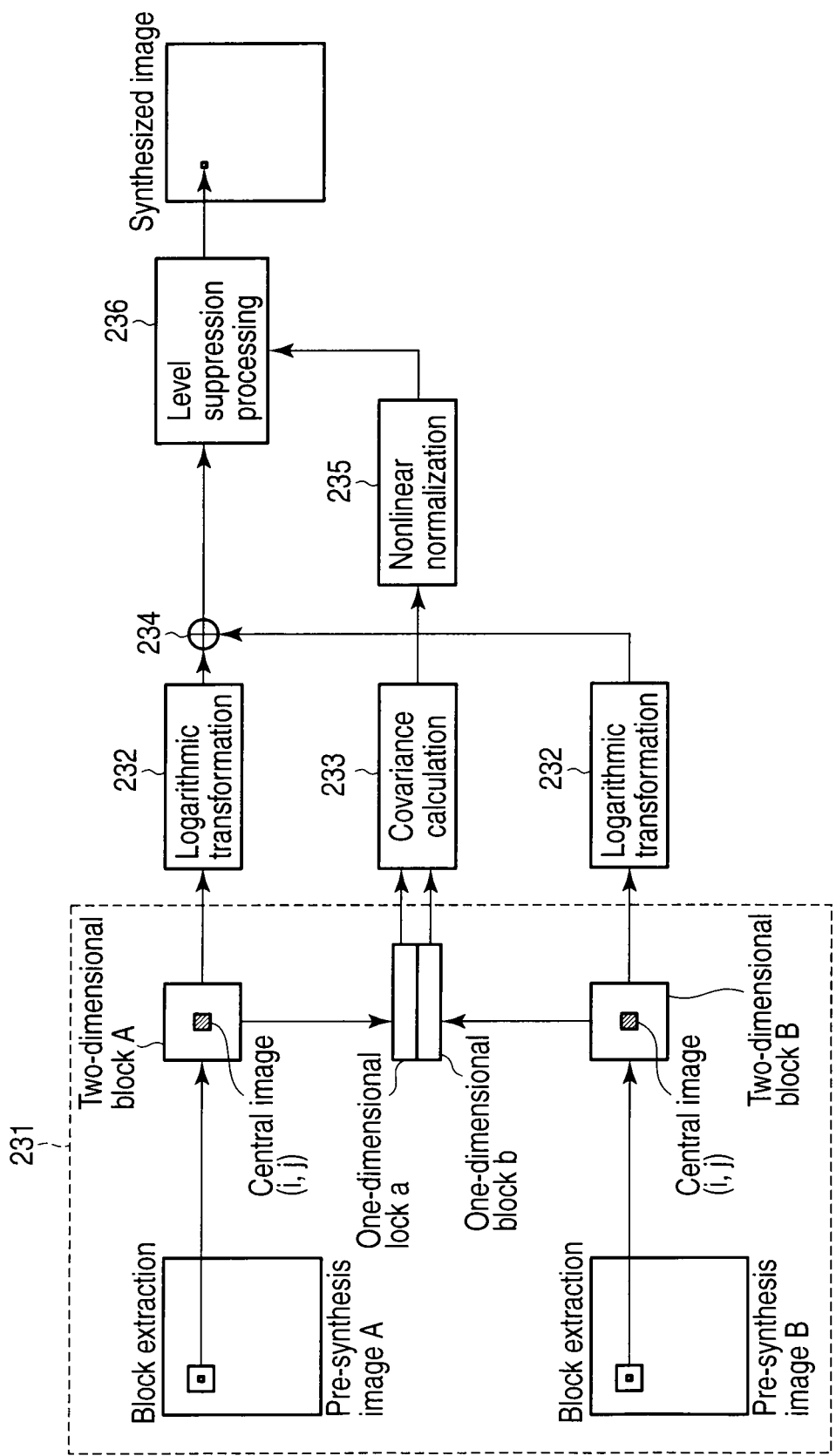
FIG. 3 is a conceptual view for explaining a procedure for noise reduction processing using covariances according to the first embodiment.

Certain embodiments provide an ultrasonic diagnostic apparatus including: a data acquisition unit configured to acquire a plurality of spatially overlapping ultrasonic images or a plurality of temporarily consecutive ultrasonic images; a block extraction unit configured to extract, for each pixel, a block having a predetermined size and including each pixel as a central pixel for each of the plurality of ultrasonic images; a covariance calculation unit configured to calculate a covariance for each pixel of each of the plurality of ultrasonic images by using the block for each pixel; and a generating unit configured to generate a synthesized image using the plurality of ultrasonic images and to control a level of each pixel of the synthesized image based on a covariance of each pixel of each of the plurality of ultrasonic images.

Note that the same reference numerals denote constituent elements having almost the same functions and arrangements in the following description, and a repetitive description will be made only when required.

FIG. 1 is a block diagram showing the arrangement of an ultrasonic diagnostic apparatus according to the first embodiment. As shown in FIG. 1, an ultrasonic diagnostic apparatus 11 includes an ultrasonic probe 12, an input device 13, a monitor 14, an ultrasonic transmission unit 21, an ultrasonic reception unit 22, a B mode processing unit 23, a Doppler processing unit 25, an image generating unit 26, an image synthesizing unit 27, a control processor (CPU) 28, an internal storage unit 29, an interface unit 30, and image memory 31. The function of each constituent element will be described below.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers. When ultrasonic waves are transmitted from the ultrasonic probe 12 to an object P, the transmitted ultrasonic waves are sequentially reflected by the discontinuity surface of acoustic impedance of an internal body tissue, and are received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The ultrasonic probe 12 of this ultrasonic apparatus may be a probe capable of performing ultrasonic scanning on a three-dimensional region of an object. In this case, the ultrasonic probe 12 has, for example, an arrangement to perform ultrasonic scanning on a three-dimensional region by mechanically swinging transducers along a direction perpendicular to the array direction of the transducers or an arrangement to perform ultrasonic scanning on a three-dimensional region by electrical control using two-dimensional transducers arrayed two-dimensionally. When the ultrasonic probe 12 adopts the former arrangement, the swinging circuit performs three-dimensional scanning on the object. An examiner can therefore automatically acquire a plurality of two-dimensional tomograms by only bringing the probe body into contact with the object. It is also possible to detect the accurate distance between slices from a controlled swinging velocity. When the ultrasonic probe 12 adopts the latter arrangement, it is theoretically possible to perform ultrasonic scanning on a three-dimensional region in the same time as that required to acquire a conventional two-dimensional tomogram.

The input device 13 includes various types of switches, buttons, a trackball, a mouse, and a keyboard which are used to input, to the apparatus body 11, various types of instructions and conditions, an instruction to set a region of interest (ROI), various types of image quality condition setting instructions, and the like from an operator. When, for example, the operator operates the end button or FREEZE button of the input device 13, the transmission/reception of ultrasonic waves is terminated, and the ultrasonic diagnostic apparatus is set in a temporary stop state.

The monitor 14 displays morphological information (B mode images) in the living body, blood flow information (an average velocity image, variance image, power image, and the like), and their combinations as images based on video signals from the image synthesizing unit 27.

The ultrasonic transmission unit 21 includes a trigger generating circuit, delay circuit, and pulser circuit (none of which are shown). The pulser circuit repeatedly generates rate pulses for the formation of transmission ultrasonic waves at a predetermined rate frequency fr Hz (period: 1/fr sec). The delay circuit gives each rate pulse the delay time required to focus ultrasonic waves into a beam for each channel and determine a transmission directivity. The trigger generating circuit applies a driving pulse to the probe 12 at the timing based on this rate pulse.

The ultrasonic reception unit 22 includes an amplifier circuit, A/D converter, and adder (none of which are shown). The amplifier circuit amplifies echo signals received via the ultrasonic probe 12 on a channel basis. The A/D converter gives each amplified echo signal the delay time required to determine a reception directivity. The adder then performs addition processing. With this addition, the reflection component of the echo signal from the direction corresponding to the reception directivity is enhanced, and a synthetic beam for ultrasonic transmission/reception is formed in accordance with the reception directivity and transmission directivity.

The B mode processing unit 23 receives the echo signal from the ultrasonic transmission unit 21, and generates data whose signal strength is represented by a brightness level. The B mode processing unit 23 transmits this data to the image generating unit 26. The monitor 14 then displays the data as a B mode image representing the strength of a reflected wave as a brightness. In particular, the B mode processing unit 23 has a noise reduction function using covariances (to be described later).

FIG. 2 is a block diagram showing an example of the arrangement of the B mode processing unit 23 to implement a noise reduction function using covariances. As shown in FIG. 2, the B mode processing unit 23 includes an envelope detection processing unit 230, a block extraction processing unit 231, a logarithmic transformation processing unit 232, a covariance calculation processing unit 233, an adding/averaging processing unit 234, a nonlinear normalization processing unit 235, and a level suppression processing unit 236. These processing units can also be implemented by hardware or software.

The envelope detection processing unit 230 executes envelope detection processing for each echo signal (IQ signal) from the ultrasonic reception unit 22, extracts the amplitude information (i.e., the luminance information) of each echo signal, and generates ultrasonic image data as the spatial distribution of the amplitude information (or the luminance information).

The block extraction processing unit 231 extracts a block including a central pixel (or a central position) and neighboring pixels (or positions) for each pixel (or each position) of each of a plurality of spatially overlapping ultrasonic image data or temporarily consecutive ultrasonic image data used for reduction processing for noise or the like. The block extraction processing unit 231 sends out each extracted block to the covariance calculation processing unit 233.

The logarithmic transformation processing unit 232 generates a logarithmic luminance signal by executing logarithmic transformation for each signal output from the envelope detection processing unit 230 or the block extraction processing unit 231. The logarithmic transformation processing unit 232 sends out the generated logarithmic luminance signal to the adding/averaging processing unit 234.

The covariance calculation processing unit 233 calculates a covariance for each central pixel included in each block by using each block. This calculation will be described in detail later.

The adding/averaging processing unit 234 adds/averages the logarithmic luminance signals of a plurality of ultrasonic images for each pixel at a corresponding spatial position to generate a synthesized image including a plurality of ultrasonic images added together.

The nonlinear normalization processing unit 235 executes nonlinear normalization processing of the covariance for each central pixel calculated by the covariance calculation processing unit 233. This calculation will be described in detail later.

The level suppression processing unit 236 executes level control for each pixel of the synthesized image, generated by the adding/averaging processing unit 234, based on the nonlinearly normalized covariance for each central pixel, thereby generating a synthesized image level-controlled for each pixel.

The Doppler processing unit 25 frequency-analyzes velocity information from the echo signal received from the transmission unit 21 to extract a blood flow, tissue, and contrast medium echo component by the Doppler effect, and obtains blood flow information such as an average velocity, variance, and power.

In general, the image generating unit 26 generates an ultrasonic diagnostic image as a display image by converting (scan conversion) the scanning line signal string for ultrasonic scanning into a scanning line signal string in a general video format typified by a TV format.

In addition, the image generating unit 26 executes various kinds of image processing other than scan conversion. That is, the image generating unit 26 executes, for example, a method (smoothing processing) of regenerating an average luminance value image using a plurality of image frames after scan conversion, a method (edge enhancement) using a differential filter within an image, and processing (three-dimensional image reconstruction) such as volume rendering using a three-dimensional reconstruction algorithm. Note that data before it is input to the image generating unit 26 is sometimes called "raw data".

The image synthesizing unit 27 synthesizes the image received from the image generating unit 26 with character information of various types of parameters, scale marks, and the like, and outputs the resultant signal as a video signal to the monitor 14.

The control processor 28 has a function as an information processing apparatus (computer) and controls the operation of the main body of the ultrasonic diagnostic apparatus. The control processor 28 reads out a dedicated program for implementing a noise reduction function using covariances and a control program for executing predetermined image generating/display operation and the like from the internal storage unit 29, and expands the programs in its own memory, thereby executing computation/control and the like associated with various kinds of processing.

The internal storage unit 29 stores a data group including dedicated programs for implementing a predetermined scan sequence, a noise reduction function using covariances according to each embodiment, and the like, control programs for executing image generation and display processing, diagnosis information (a patient ID, findings by a doctor, and the like), a diagnosis protocol, and transmission/reception conditions. This storage unit is also used to, for example, archive images in the image memory (not shown). Data in the internal storage unit 29 can be transferred to an external peripheral apparatus via the interface unit 30.

The interface unit 30 is a circuit associated with the input device 13, a network, and a new external storage device (not shown). The interface unit 30 can transfer data such as ultrasonic images, analysis results, and the like obtained by this apparatus to another apparatus via a network.

The image memory 31 stores ultrasonic images temporarily.

(Noise Reduction Function Using Covariances)

The noise reduction function of the ultrasonic diagnostic apparatus 1 which uses covariances will be described next. As in the spatial compound method, persistence method, and the like, when one image is to be generated by synthesizing a plurality of spatially overlapping images or temporarily consecutive images, this function calculates a covariance for each pixel, evaluating the noise level of each pixel by using the covariance, and controls a signal level for each pixel based on the evaluation result.

FIG. 3 is a conceptual view for explaining a procedure for noise reduction processing (especially spatial compound processing) using covariances, which is executed by the B mode processing unit 23. Processing (noise reduction processing using covariances) based on the noise reduction function using covariance will be described below with reference to FIGS. 2 and 3. For the sake of descriptive simplicity, assume that two ultrasonic images are to be used in spatial compound processing in the following description and each embodiment. However, this is merely an example, and the present embodiment is not limited to the number of ultrasonic images used in spatial compound processing.

As shown in FIG. 3, first of all, the logarithmic transformation processing unit 232 logarithmically transforms two ultrasonic images (to be referred to a pre-synthesis image A and a pre-synthesis image B) as the spatial distributions of luminance signals. The adding/averaging processing unit 234 then generates a synthesized image by adding pixels at corresponding spatial positions. Note that the pre-synthesis image A and the pre-synthesis image B are acquired by performing ultrasonic scanning a plurality of number of times so as to make identical regions of the object overlap at least partly while changing the reception aperture with respect to the same transmission.

On the other hand, concurrently with the generation of a synthesized image by the above addition processing, as shown in FIG. 3, when the envelope detection processing unit 230 inputs the pre-synthesis image B to the block extraction processing unit 231, the block extraction processing unit 231 extracts two-dimensional blocks A(i, j) and B(i, j), each having a size of P×Q=N pixels and including a central pixel (i, j) and surrounding pixels, for each pixel of the pre-synthesis image A and pre-synthesis image B. The block extraction processing unit 231 also generates one-dimensional blocks a(i, j) and b(i, j) each having a length of N pixels from the respective extracted two-dimensional blocks.

The covariance calculation processing unit 233 calculates the covariances of the two-dimensional blocks A(i, j) and B(i, j) associated with the central pixel (i, j) (i.e., the position (i, j) on the image) by using the input one-dimensional blocks a(i, j) and b(i, j).

That is, letting $I_A(i, j)$ be the pixel value of the central pixel included in the one-dimensional block a(i, j) (or the two-dimensional block A(i, j) or B(i, j)) and $I_B(i, j)$ be the pixel value of the central pixel included in the one-dimensional block b(i, j), the covariance between the two-dimensional blocks A(i, j) and B(i, j) is calculated by equation (1) given below. Note that $I_{BlkA}(i, j)$ and $I_{BlkB}(i, j)$ respectively represent sets of pixel values (luminance values) of the respective pixels included in the two-dimensional blocks A(i, j) and B(i, j). In addition, E[x] represents the expected value of x. Therefore, $E[I_{BlkA}(i, j)]$ represents the expected value of a pixel value included in the one-dimensional block a(i, j) (or the two-dimensional block A(i, j)).

$$I_{Cov} = \text{cov}[I_{BlkA}(i, j), I_{BlkB}(i, j)] \quad (1)$$
$$= E[\{I_A(i, j) - E[I_{BlkA}(i, j)]\}\{I_B(i, j) - E[I_{BlkB}(i, j)]\}]$$

The calculated covariances are sent out to the nonlinear normalization processing unit 235. The absolute values of the covariances calculated by the covariance calculation processing unit 233 do not have any upper limit. For this reason, the nonlinear normalization processing unit 235 performs nonlinear normalization at the position (i, j) on the image according to equation (2) given below. This nonlinear normalization can make the value output to the level suppression processing unit 236 on the subsequent stage fall within the range from 0 to 1, based on the covariance.

$$\beta(i, j) = 1 - \exp\left(-\frac{|I_{Cov}(i, j)|}{\alpha}\right) \quad (2)$$

Note that the nonlinear normalization based on equation (2) is merely an example. This embodiment is not limited to this example, and may use, for example, a combination of a simple linear function and saturation processing.

The level suppression processing unit 236 calculates an output level at the pixel (i, j) (i.e., the position (i, j) of the image) according to equation (3):

$$I_{Out}(i, j) = \frac{I_A(i, j) + I_B(i, j)}{2} \cdot \{\gamma \cdot \beta(i, j) + (1 - \gamma)\} \quad (3)$$

where $I_{Out}$ represents an image output, and γ represents the degree at which a covariance is made to act on an averaged image (no action when 0≤γ≤1 and γ=0).

Level control using covariances described above is executed for all the positions (all pixels) on an image. As a result, a synthesized image is generated, in which level suppression is performed in accordance with the covariances. The image generating unit 26 scan-converts the generated synthesized image. The image synthesizing unit 27 synthesizes the image with predetermined information. The monitor 14 then displays the synthesized image in a predetermined form.

Figures 4A, 4B, 4C:
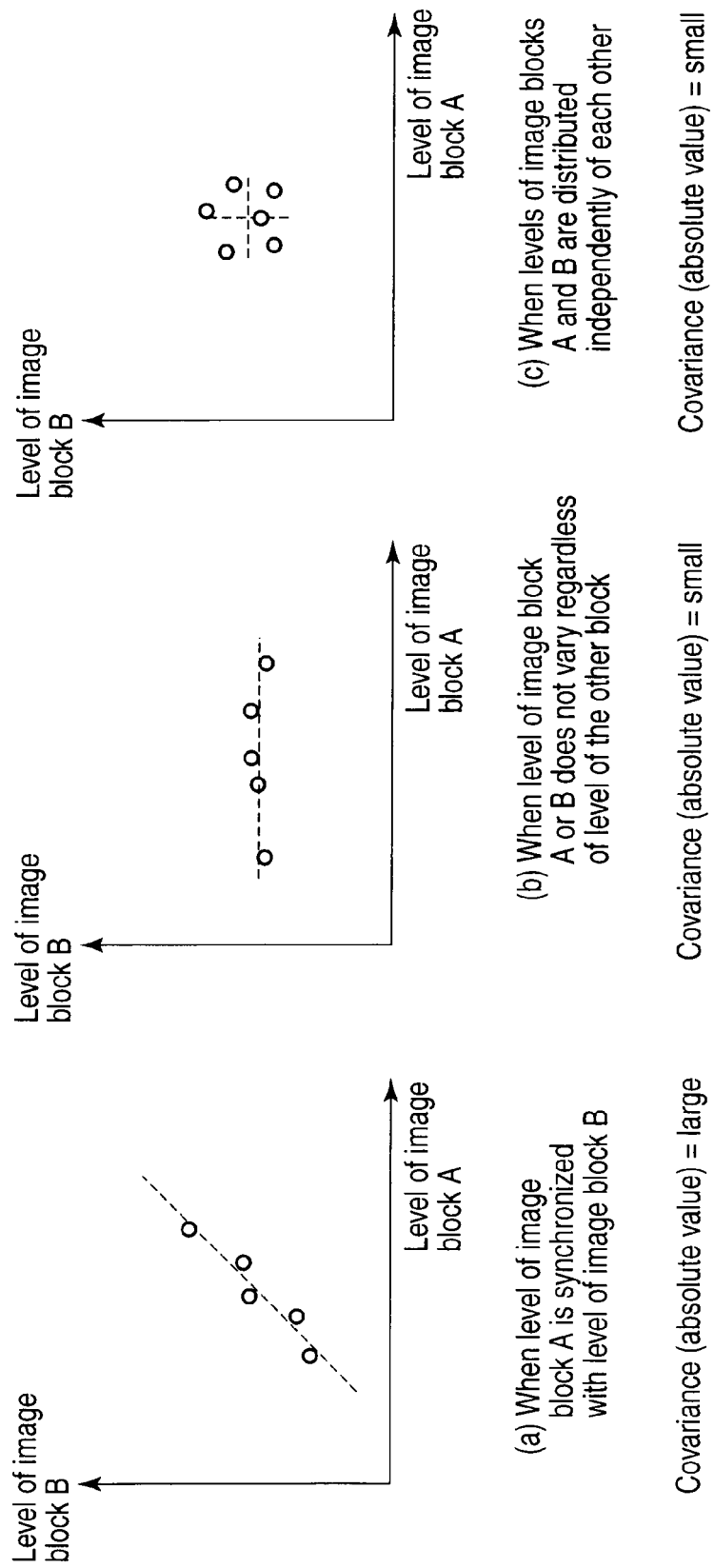
FIGS. 4A, 4B, and 4C are views for explaining a mechanism which can reduce noise by noise reduction processing using covariances.

FIGS. 4A, 4B, and 4C are graphs for explaining a mechanism which can reduce noise by this noise reduction processing using covariances.

As indicated in FIG. 4A, when the level of the two-dimensional block A(i, j) links with the level of the two-dimensional block B(i, j), the absolute value of the covariance is relatively large. In contrast, as indicated in FIG. 4B, when one of the levels of the two-dimensional blocks A(i, j) and B(i, j) does not vary regardless of the level of the other two-dimensional block, the absolute value of the covariance is relatively small. In addition, as indicated in FIG. 4C, when the levels of the two-dimensional blocks A(i, j) and B(i, j) are distributed irrespectively of each other, the absolute value of the covariance is relatively small. Therefore, the absolute values of the covariances of noise and portions irrespective of each other are small, and hence the noise level can be suppressed by suppressing the levels of portions exhibiting small absolute values of covariances.

When generating one image by synthesizing a plurality of spatially overlapping images or temporarily consecutive images as in the spatial compound method, persistence method, or the like, the ultrasonic diagnostic apparatus described above calculates a covariance for each (central) pixel and evaluates the noise level of each pixel by using the covariance. This apparatus calculates a signal level to be output for each pixel based on the evaluation result, thereby controlling noise reduction depending on how noise is superimposed on each pixel. As a consequence, this method can reduce noise properly and efficiently in accordance with the degree of occurrence of noise at each position on an image as compared with the conventional method of reducing noise by only addition processing.

Second Embodiment

The first embodiment has exemplified the case in which the apparatus uses the covariances of the ultrasonic images A and B before synthesis in the spatial compound method such that it suppresses the noise of a portion exhibiting a small covariance. In contrast to this, an ultrasonic diagnostic apparatus according to the second embodiment suppresses noise properly and efficiently in accordance with the degree of generation of noise at each position on an image by using correlation coefficients in place of covariances.

FIG. 5 is a block diagram showing an example of the arrangement of a B mode processing unit 23 to implement a noise reduction function using correlation coefficients according to the second embodiment. This arrangement differs from that shown in FIG. 2 in that it includes a correlation coefficient calculation processing unit 237 in place of the covariance calculation processing unit 233, and does not include the nonlinear normalization processing unit 235.

In general, letting $\sigma_x$ and $\sigma_y$ be the standard deviations of random variables x and y and cov[x, y] be the covariance of x and y, a correlation coefficient $\rho_{xy}$ is expressed by $$\rho_{xy} = \frac{\text{cov}[x, y]}{\sigma_x \sigma_y} \quad (4)$$

A correlation coefficient differs from a covariance in that the correlation coefficient is normalized between −1 and 1. That is, when using a correlation coefficient for noise suppression, it is not necessary to perform special computation for normalization as in the first embodiment except for the calculation of an absolute value.

The correlation coefficient calculation processing unit 237 calculates the correlation coefficients of two-dimensional blocks A(i, j) and B(i, j) at a pixel (i, j) (i.e., a position (i, j) on the image) by using one-dimensional blocks a(i, j) and b(i, j) output from a block extraction processing unit 231 according to equation (5) given below:

$$\rho = \frac{\text{cov}[I_{BlkA}(i,\, j),\, I_{BlkB}(i,\, j)]}{\sigma_{BlkA(i,j)} \sigma_{BlkB(i,j)}} \quad (5)$$

where $\sigma_{BlkA}(i,j)$ and $\sigma_{BlkB}(i,j)$ be the standard deviations of the correlation coefficients of the two-dimensional blocks A(i, j) and B(i, j).

A level suppression processing unit 236 calculates an output level at the position (i, j) on the image (i.e., the pixel (i, j)) according to equation (6):

$$I_{Out}(i,\, j) = \frac{I_A(i,\, j) + I_B(i,\, j)}{2} \cdot \{\gamma \cdot |\rho(i,\, j)| + (1 - \gamma)\} \quad (6)$$

Note that equation (6) corresponds to equation (3) in the first embodiment.

It is possible to explain, from the definition of a correlation coefficient, the reason why noise can be reduced by using correlation coefficients, as in the case of covariances. That is, when the level of the two-dimensional block A(i, j) is synchronized with the level of the two-dimensional block B(i, j), the absolute value of the correlation coefficient is relatively large. When one of the levels of the two-dimensional blocks A(i, j) and B(i, j) does not vary regardless of the level of the other two-dimensional block, the absolute value of the correlation coefficient is relatively small. In addition, when the levels of the two-dimensional blocks A(i, j) and B(i, j) are distributed irrespectively of each other, the absolute value of the correlation coefficient is relatively small. Therefore, the absolute values of the correlation coefficients of noise and portions not associated with each other are small, and hence the noise level can be suppressed by suppressing the levels of portions exhibiting small absolute values of correlation coefficients.

The above arrangement can also obtain nearly the same effects as those of the first embodiment.

Third Embodiment

The first and second embodiments have exemplified the case in which the apparatus uses the covariances or correlation coefficients of a plurality of pre-synthesis images in the spatial compound method such that it suppresses the noise of a portion exhibiting a small covariance or correlation coefficient. In these embodiments, image data for the calculation of covariances or correlation coefficients are luminance values after envelope detection.

In contrast to this, it is also possible to suppress noise by calculating and using complex covariances or complex correlation coefficients from IQ signals before envelope detection. The third embodiment will therefore exemplify a case in which the complex covariances of a plurality of pre-synthesis images in the spatial compound method such that the noise of a portion exhibiting a small complex covariance.

FIG. 6 is a block diagram showing an example of the arrangement of a B mode processing unit 23 to implement a noise reduction function using covariances according to the third embodiment. This arrangement differs from that shown in FIG. 2 in that it includes a complex covariance calculation processing unit 238 in place of the covariance calculation processing unit 233. In addition, these arrangements differ in the position of the block extraction processing unit 231.

Figure 7:
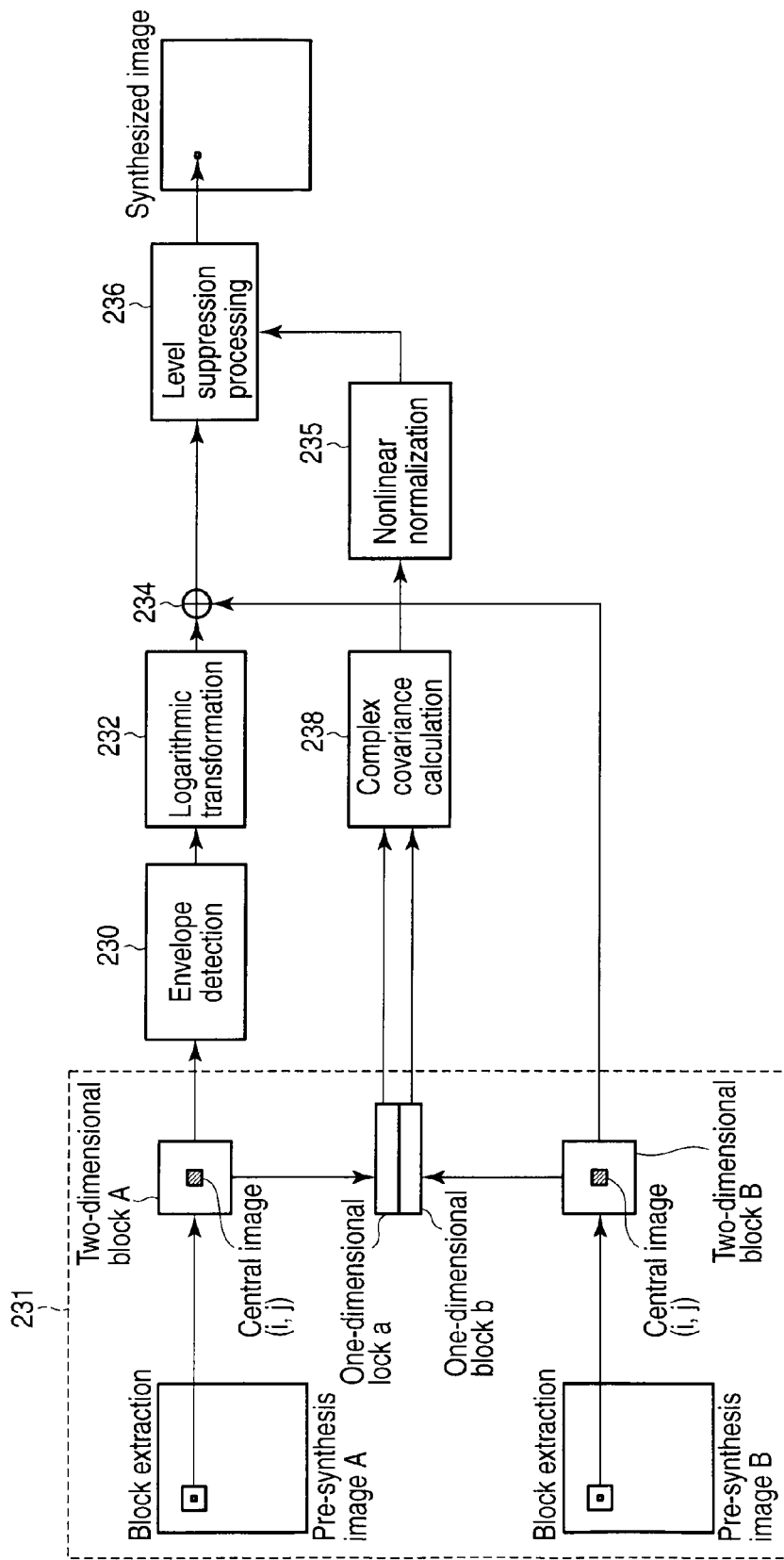
FIG. 7 is a conceptual view for explaining a procedure for spatial compound processing according to the third embodiment.

FIG. 7 is a conceptual view for explaining a procedure for spatial compound processing according to this embodiment. This procedure differs from that shown in FIG. 3 in that each processing unit for real-number computation is replaced with a processing unit for complex-number computation. Complex IQ signals are input to an envelope detection processing unit 230 and also input to the block extraction processing unit 231. The block extraction processing unit 231 or the like is the same as the image block extraction unit 240 in the first and second embodiments except that the block extraction processing unit 231 handles complex numbers instead of real numbers.

The complex covariance calculation processing unit 238 calculates the complex covariances of complex random variables z1 and z2 by using complex conjugation according to equation (7):

$$\text{cov}[z_1, z_2] = E[\{z_1 - E[z_1]\}\{z_2 - E[z_2]\}^*] \quad (7)$$

In this case, a complex covariance cov[z1, z2] is conjugate to a complex covariance cov[z2, z1]. The two complex covariances can be made to have the same value by calculating their absolute values afterward. It is therefore possible to perform calculation using either of the complex covariances.

A nonlinear normalization processing unit 235 executes calculation for nonlinear normalization as in the first and second embodiments. Note that this calculation is essentially the same as that represented by equation (2) except that a complex covariance is input.

A level suppression processing unit 236 calculates an output level at a position (i, j) (i.e., a pixel (i, j)) on the image according to equation (3) given below.

The operation and effect in noise reduction are the same as those when an original image is constituted by real luminance values. This apparatus extracts blocks of the respective images in the form of IQ signals before detection for a plurality of pre-synthesis images in the spatial compound method, and evaluates the noise level of each pixel. Calculating a signal level output for each pixel based on the evaluation result will control noise reduction in accordance with how noise is superimposed on each pixel (in particular, suppressing the level of a portion exhibiting a small absolute value of a complex covariance will control noise reduction). As a consequence, this method can reduce noise properly and efficiently in accordance with the degree of generation of noise at each position on an image as compared with the conventional method of reducing noise by only addition processing.

Fourth Embodiment

The fourth embodiment will exemplify a case in which noise is suppressed by using the complex correlation coefficients of IQ signal images as in the second embodiment configured to reduce noise by using the real correlation coefficients of luminance signal images.

Figure 8:
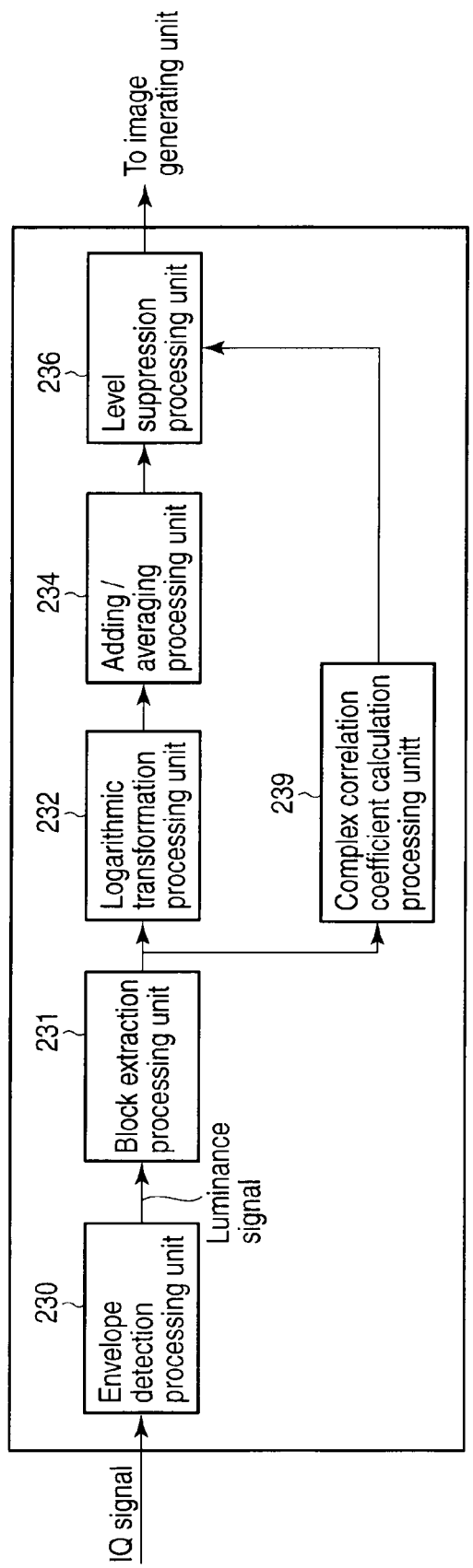
FIG. 8 is a block diagram showing an example of the arrangement of a B mode processing unit 23 to implement a noise reduction function using complex correlation coefficients according to the fourth embodiment.

FIG. 8 is a block diagram showing an example of the arrangement of a B mode processing unit 23 to implement a noise reduction function using complex correlation coefficients according to the fourth embodiment. This arrangement differs from that shown in FIG. 5 in that it includes a complex correlation coefficient calculation processing unit 239 in place of the correlation coefficient calculation processing unit 237.

Figure 9:
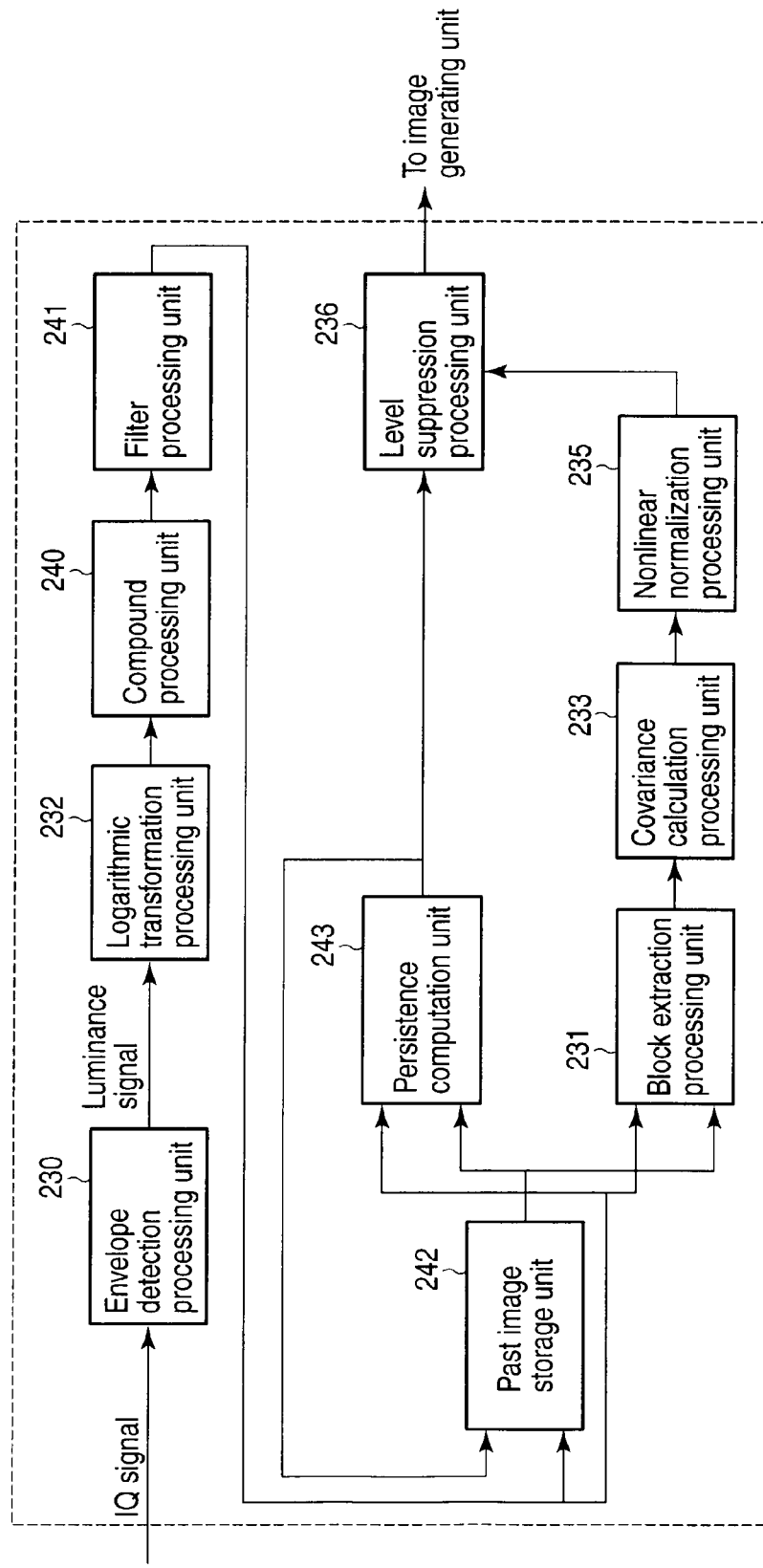
FIG. 9 is a block diagram showing an example of the arrangement of a B mode processing unit 23 to implement a noise reduction function using covariances according to the fifth embodiment.

FIG. 9 is a conceptual view for explaining a procedure for spatial compound processing according to this embodiment.

The complex correlation coefficient calculation processing unit 239 calculates a complex correlation coefficient according to equation (8) given below:

$$\rho_z = \frac{\text{cov}[z_1, z_2]}{\sigma_{z1}\sigma_{z2}} \qquad (8)$$

$$\sigma_{zi} = \sqrt{|\text{var}[z_i]|} = \sqrt{|\text{cov}[z_i, z_i]|}$$

where var[zi] is the complex covariance of zi (i=1, 2).

Although a complex correlation coefficient is a complex number, its absolute value is normalized within the range of 0 to 1. Using the absolute value of a complex correlation coefficient makes the subsequent processing procedure the same as that in the second embodiment.

The operation and effect in noise reduction are the same as those when an original image is constituted by real luminance values. This apparatus extracts blocks of the respective images in the form of IQ signals before detection for a plurality of pre-synthesis images in the spatial compound method, and suppresses the levels of portions exhibiting small absolute values of these complex correlation coefficients, thereby suppressing noise. As a consequence, it is possible to reduce noise more efficiently than the conventional method of synthesizing images by only addition.

Fifth Embodiment

The first to fourth embodiments are configured to suppress levels by using covariances or correlation coefficients of a plurality of spatially overlapping images. In contrast to this, the fifth embodiment is configured to suppress levels by using the covariances or correlation coefficients of a plurality of temporarily consecutive images, as will be described below. For the sake of concreteness, the following description will exemplify a case in which covariances are calculated and used as the real numbers of a plurality of temporarily consecutive images. Obviously, this embodiment is not limited to covariances as the real numbers, and it is possible to implement proper level suppression by using any of the following values as the real numbers: correlation coefficients, complex covariances, and complex correlation coefficients of a plurality of temporarily consecutive images as real numbers.

FIG. 9 is a block diagram showing an example of the arrangement of a B mode processing unit 23 to implement a noise reduction function using covariances according to the fifth embodiment. This arrangement differs from that shown in FIG. 2 in that it further includes a compound processing unit 240, a filter processing unit 241, a past image storage unit 242, and a persistence computation unit 243.

An envelope detection processing unit 230 executes envelope detection for the echo signal output from an ultrasonic reception unit 22, and outputs the amplitude component of a luminance signal (i.e., an IQ signal) after the detection to a logarithmic transformation processing unit 232. The logarithmic transformation processing unit 232 performs logarithmic transformation processing for the amplitude component of each signal output from the envelope detection processing unit 230, and outputs the resultant logarithmic luminance signal to the compound processing unit 240.

The compound processing unit 240 performs signal synthesis processing such as spatial compound processing. It is also possible to execute noise reduction processing described in the first to fourth embodiments in addition to the above processing, as needed.

The filter processing unit 241 executes noise reduction such as spike noise removal by using a spatial filter.

The past image storage unit 242 stores a past image to be used for persistence computation executed by the persistence computation unit 243. The past image to be stored is either the image supplied from the filter processing unit 241 or the image fed back from an output from the persistence computation unit 243.

The persistence computation unit 243 executes persistence computation for the removal of noise and speckle which change temporarily by using the current and past images (a plurality of temporarily consecutive images) in the following manner.

That is, letting $I_{In}(tn)$ be an input image at current time tn and $I_{Out}(tn)$ be an image after computation, the persistence computation unit 243 executes typical persistence computation according to equation (9):

$$I_{Out(m)} = (1-a)I_{In(m)} + aI_{Out(m-1)} \qquad (9)$$

The persistence computation unit 243 synthesizes the current image and the immediately preceding image to generate an image after the computation. The generated image is used as the immediately preceding image at the next time. In this manner, the persistence computation unit 243 reduces temporal changes in noise and speckle in the image and outputs the resultant image.

Figure 10:
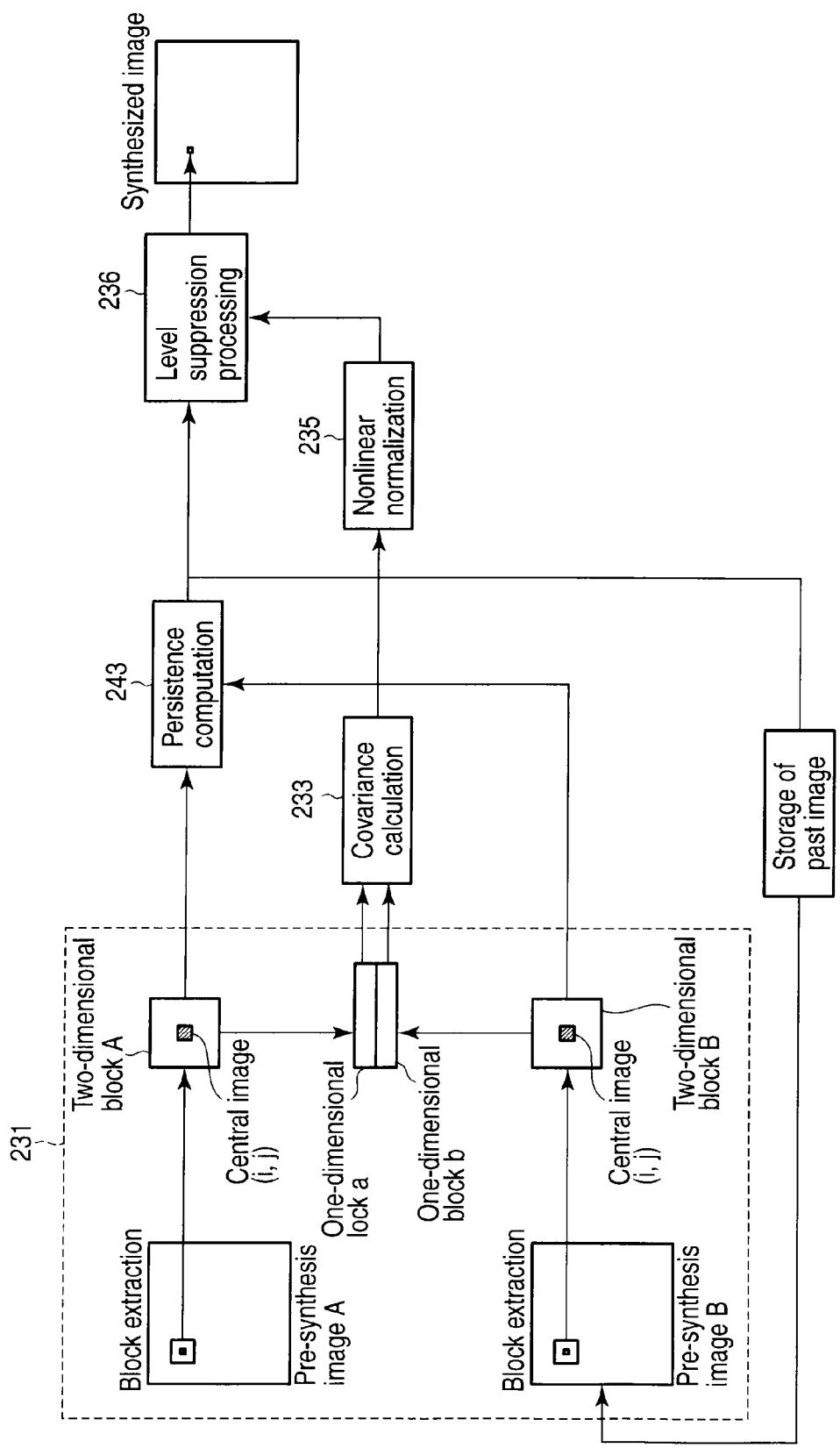
FIG. 10 is a conceptual view for explaining a procedure for noise reduction processing using covariances according to the fifth embodiment.

FIG. 10 is a conceptual view for explaining a procedure for noise reduction processing using covariances according to the fifth embodiment. As shown in FIG. 10, a block extraction processing unit 231 executes block extraction processing described in the first embodiment upon setting, for example, the current image before persistence processing as an image Tn, and the past image immediately preceding the current image as an image Tn–1. A covariance calculation processing unit 233 calculates a covariance for each pixel by using one-dimensional blocks of the images Tn and Tn–1. A nonlinear normalization processing unit 235 performs nonlinear normalization at a position (i, j) on the image according to equation (2) described above. A level suppression processing unit 236 calculates an output level at the position (i, j) on the image (i.e., the pixel (i, j)) according to equation (3) described above.

The above arrangement can suppress noise by suppressing the levels of portions, of image blocks of a plurality of current and past images in persistence processing, which exhibit small absolute values of covariances. As a consequence, this method can reduce noise properly and efficiently in accordance with the degree of occurrence of noise at each position on an image as compared with the conventional method of reducing noise by only addition processing.

Sixth Embodiment

The first to fifth embodiments each have exemplified the case in which level suppression is performed for a plurality of spatially overlapping two-dimensional image data or temporarily consecutive two-dimensional image data. The method described in each embodiment can also be applied to a plurality of spatially overlapping three-dimensional image data (volume data) or temporarily consecutive three-dimensional image data. The sixth embodiment will exemplify a case in which the method described in the first embodiment is applied to three-dimensional image data. Each method according to the second to fifth embodiments can be extended in the same manner as described in this embodiment.

FIG. 11 is a conceptual view for explaining a procedure for noise reduction processing (especially spatial compound processing) using the covariance of three-dimensional image data, which is executed by a B mode processing unit 23. Processing based on a noise reduction function using covariances (noise reduction processing using covariances) will be described with reference to FIGS. 2 and 11. For the sake of descriptive simplicity, assume that two three-dimensional image data (volume data) are to be used in spatial compound processing. However, this is merely an example. It is possible to arbitrarily set the number of volume data to be used for spatial compound processing.

As shown in FIG. 11, a logarithmic transformation processing unit 232 logarithmically transforms two volume data (to be referred to as pre-synthesis volume data C and pre-synthesis volume data D) as the spatial distributions of luminance signals. An adding/averaging processing unit 234 then adds voxels whose spatial positions correspond to each other, thereby generating synthesized volume data. Note that the pre-synthesis volume data C and the pre-synthesis volume data D are acquired by performing ultrasonic scanning a plurality of number of times so as to make identical three-dimensional regions of the object overlap at least partly while changing the reception aperture with respect to the same transmission.

On the other hand, concurrently with the generation of synthesized volume data by the above addition processing, as shown in FIG. 11, when an envelope detection processing unit 230 inputs the pre-synthesis volume data C and the pre-synthesis volume data D to a block extraction processing unit 231, the block extraction processing unit 231 extracts three-dimensional blocks C(i, j, k) and D(i, j, k), each having a size of P·Q·R=M voxels and including a central voxel (i, j, k) and surrounding voxels, for each voxel of the pre-synthesis volume data C and the pre-synthesis volume data D. The block extraction processing unit 231 also generates one-dimensional blocks c(i, j, k) and d(i, j, k) each having a length of M voxels from the respective extracted three-dimensional blocks, and sends out the generated one-dimensional blocks to the covariance calculation processing unit 233.

The covariance calculation processing unit 233 calculates the covariances of the three-dimensional blocks C(i, j, k) and D(i, j, k) associated with the central voxel (i, j, k) (i.e., the position (i, j, k) on the volume data) by using the input one-dimensional blocks c(i, j, k) and d(i, j, k).

That is, letting $I_C(i, j, k)$ be the value of the central voxel included in the one-dimensional block c(i, j, k) (or the three-dimensional block C(i, j, k)) and $I_D(i, j, k)$ be the value of the central pixel included in the one-dimensional block d(i, j, k) (or the three-dimensional block D(i, j, k)), the covariance between the three-dimensional blocks C(i, j, k) and D(i, j, k) is calculated by equation (10) given below. Note that $I_{BlkC}(i, j, k)$ and $I_{BlkD}(i, j, k)$ respectively represent sets of values (luminance values) of the respective voxels included in the three-dimensional blocks C(i, j, k) and D(i, j, k). In addition, E[x] represents the expected value of x. Therefore, $E[I_{BlkC}(i, j, k)]$ represents the expected value of the voxel value included in the one-dimensional block c(i, j, k) (or the three-dimensional block C(i, j, k)).

$$I_{Cov} = \text{cov}[I_{BlkC}(i, j, k), I_{BlkD}(i, j, k)] \quad (10)$$
$$= E[\{I_C(i, j, k) - E[I_{BlkC}(i, j, k)]\}\{I_D(i, j, k) - E[I_{BlkD}(i, j, k)]\}]$$

The calculated covariances are sent out to a nonlinear normalization processing unit 235. The absolute values of the covariances calculated by the covariance calculation processing unit 233 do not have any upper limit. For this reason, the nonlinear normalization processing unit 235 performs nonlinear normalization at the position (i, j, k) on the volume data according to equation (11) given below. This nonlinear normalization can make the value output to a level suppression processing unit 236 on the subsequent stage fall within the range from 0 to 1, based on the covariance.

$$\beta(i, j, k) = 1 - \exp\left(-\frac{|I_{Cov}(i, j, k)|}{\alpha}\right) \quad (11)$$

Note that the nonlinear normalization based on equation (11) is merely an example. The present embodiment is not limited to this example, and may use, for example, a combination of a simple linear function and saturation processing.

The level suppression processing unit 236 calculates an output level at the voxel (i, j, k) (i.e., the position (i, j, k) on the volume data) according to equation (12):

$$I_{Out}(i, j, k) = \frac{I_C(i, j, k) + I_D(i, j, k)}{2} \cdot \{\gamma \cdot \beta(i, j, k) + (1 - \gamma)\} \quad (12)$$

where $I_{Out}$ represents an image output, and γ represents the degree at which a covariance is made to act on an added/averaged image (no action when 0≤γ≤1 and γ=0).

Level control using covariances described above is executed for all the positions (all voxels) on volume data. As a result, synthesized volume data is generated, in which level suppression is performed in accordance with the covariances. An image generating unit 26 scan-converts the generated synthesized volume data. An image synthesizing unit 27 synthesizes the volume data with predetermined information. A monitor 14 then displays the synthesized volume data in a predetermined form.

When generating one volume data by synthesizing a plurality of spatially overlapping volume data or temporarily consecutive volume data as in the spatial compound method, persistence method, or the like, the ultrasonic diagnostic apparatus described above calculates a covariance for each (central) voxel and evaluates the noise level of each voxel by using the covariance. This apparatus calculates a signal level to be output for each voxel based on the evaluation result, thereby controlling noise reduction depending on how noise is superimposed on each voxel. As a consequence, this method can reduce noise properly and efficiently in accordance with the degree of occurrence of noise at each position on volume data as compared with the conventional method of reducing noise by only addition processing.

Note that the present embodiment is not limited to the above embodiments, and constituent elements can be variously modified and embodied at the execution stage within the spirit and scope of the embodiment. The following are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks (Floppy®) disks, hard disks, and the like), optical disks (CD-ROMs, DVDs, and the like), and semiconductor memories.

(2) Each embodiment described above has exemplified the ultrasonic diagnostic apparatus having the noise reduction function using covariances. However, the technical idea is not limited to the ultrasonic diagnostic apparatus. That is, the present embodiment can be applied to any types of apparatuses as long as they are medical image reference apparatuses and the like typified by a medical image diagnostic apparatus, ultrasonic image processing apparatus, and medical workstation which generate one image by synthesizing a plurality of spatially overlapping images or temporarily consecutive images as in the spatial compound method, persistence method, or the like.

Various embodiments can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   a memory configured to store a first ultrasonic image and a second ultrasonic image obtained from ultrasonic scans of an object using an ultrasound probe,
   wherein each of the first and second ultrasonic images includes an overlap region indicating an identical region of the object; and
   processing circuitry configured to
   extract a first block including a plurality of pixels with respect to each position in the overlap region of the first ultrasonic image;
   extract a second block including a plurality of pixels with respect to each position in the overlap region of the second ultrasonic image;
   calculate a covariance by using values of pixels constructing each of the first and second blocks with respect to each position; and
   generate a synthesized image by using the first and second ultrasonic images so that a signal level, is suppressed in accordance with the calculated covariance.

2. The apparatus according to claim 1, wherein the first and second ultrasonic images are acquired by performing ultrasonic scanning a plurality of times so as to make identical regions of the object overlap at least partly while changing a reception aperture with respect to identical transmissions.

3. The apparatus according to claim 1, wherein the first and second ultrasonic images are constituted by luminance signals, and
   the circuitry calculates each covariance by using the luminance signals.

4. The apparatus according to claim 1, wherein the first and second ultrasonic images are not subjected to a detection process, and
   the circuitry calculates each covariance as a complex covariance.

5. An ultrasonic diagnostic apparatus, comprising:
   a memory configured to store a first three-dimensional ultrasonic image and a second three-dimensional ultrasonic image obtained from ultrasonic scans of an object using an ultrasound probe, wherein each of the first and second three-dimensional ultrasonic images includes an overlap region indicating an identical three-dimensional region of the object; and
   processing circuitry configured to
   extract a first block including a plurality of voxels with respect to each position in the overlap region of the first three-dimensional ultrasonic image;
   extract a second block including a plurality of voxels with respect to each position in the overlap region of the second three-dimensional ultrasonic image;
   calculate a covariance by using values of voxels constructing each of the first and second blocks with respect to each position; and
   generate a synthesized three-dimensional ultrasonic image by using the first and second three-dimensional ultrasonic images so that a signal level is suppressed in accordance with the calculated covariance.

6. The apparatus according to claim 5, wherein the first and second three-dimensional ultrasonic images are acquired by performing ultrasonic scanning a plurality of times so as to make identical regions of the object overlap at least partly while changing a reception aperture with respect to identical transmissions.

7. The apparatus according to claim 5, wherein the first and second three-dimensional ultrasonic images are constituted by luminance signals, and
   the circuitry calculates each covariance by using the luminance signals.

8. The apparatus according to claim 5, wherein the first and second three-dimensional ultrasonic images are not subjected to a detection process, and
   the circuitry calculates each covariance as a complex covariance.

9. An ultrasonic image processing apparatus, comprising:
   a memory configured to store a first ultrasonic image and a second ultrasonic image obtained from ultrasonic scans of an object using an ultrasound probe, wherein each of the first and second ultrasonic images includes an overlap region indicating an identical region of the object; and
   circuitry configured to
   extract a first block including a plurality of pixels with respect to each position in the overlap region of the first ultrasonic image;
   extract a second block including a plurality of pixels with respect to each position in the overlap region of the second ultrasonic image;
   calculate a covariance by using values of pixels constructing each of the first and second blocks with respect to each position; and
   generate a synthesized image by using the first and second ultrasonic images so that a signal level is suppressed in accordance with the calculated covariance.

10. The apparatus according to claim 9, wherein the first and second ultrasonic images are acquired by performing ultrasonic scanning a plurality of times so as to make identical regions of the object overlap at least partly while changing a reception aperture with respect to identical transmissions.

11. The apparatus according to claim 9, wherein the first and second ultrasonic images are constituted by luminance signals, and
    the circuitry calculates each covariance by using the luminance signals.

12. The apparatus according to claim 9, wherein the first and second ultrasonic images are not subjected to a detection process, and the circuitry calculates each covariance as a complex covariance.

13. An ultrasonic image processing apparatus, comprising:
a memory configured to store a first three-dimensional ultrasonic image and a second three-dimensional ultrasonic image obtained from ultrasonic scans of an object using an ultrasound probe, wherein each of the first and second three-dimensional ultrasonic images includes an overlap region indicating an identical three-dimensional region of the object; and
processing circuitry configured to
extract a first block including a plurality of voxels with respect to each position in the overlap region of the first three-dimensional ultrasonic image;
extract a second block including a plurality of voxels with respect to each position in the overlap region of the second three-dimensional ultrasonic image;
calculate a covariance by using values of voxels constructing each of the first and second blocks with respect to each position; and
generate a synthesized three-dimensional ultrasonic image by using the first and second three-dimensional ultrasonic images so that a signal level is suppressed in accordance with the calculated covariance.

14. The apparatus according to claim 13, wherein the first and second three-dimensional ultrasonic images are acquired by performing ultrasonic scanning a plurality of times so as to make identical regions of the object overlap at least partly while changing a reception aperture with respect to identical transmissions.

15. The apparatus according to claim 13, wherein the first and second three-dimensional ultrasonic images are constituted by luminance signals, and
the circuitry calculates each covariance by using the luminance signals.

16. The apparatus according to claim 13, wherein the first and second three-dimensional ultrasonic images are not subjected to a detection process, and
the circuitry calculates each covariance as a complex covariance.

17. The apparatus according to claim 1, wherein the circuitry executes a nonlinear normalization process of the covariance for a value of each position of each of the first and second ultrasonic images; and
the circuitry suppresses the signal level at each position by using the normalized covariance.

18. The apparatus according to claim 5, wherein the circuitry executes a nonlinear normalization process of the covariance for the value of each position of each of the first and second three-dimensional ultrasonic images; and
the circuitry suppresses the signal level at each position by using the normalized covariance.

19. The apparatus according to claim 1, wherein first and second ultrasonic images are temporally consecutive.

20. The apparatus according to claim 5, wherein first and second three-dimensional ultrasonic images are temporally consecutive.

21. An ultrasonic diagnostic apparatus, comprising:
a memory configured to store a first ultrasonic image and a second ultrasonic image obtained from ultrasonic scans of an object using an ultrasound probe; and
processing circuitry configured to
extract a block including of a plurality of pixels with respect to each position in the overlap region of each of the ultrasonic images;
calculate a covariance by using values of pixels constructing each of the blocks with respect to each position; and
generate a synthesized image by using the ultrasonic images so that a signal level is suppressed in accordance with the calculated covariance.

* * * * *